United States Patent
Alsberg et al.

(10) Patent No.: US 10,512,708 B2
(45) Date of Patent: Dec. 24, 2019

(54) BIOADHESIVE HYDROGELS

(71) Applicant: Case Western Reserve University, Cleveland, OH (US)

(72) Inventors: Eben Alsberg, Cleveland, OH (US); Oju Jeon, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 153 days.

(21) Appl. No.: 14/773,659

(22) PCT Filed: Mar. 7, 2014

(86) PCT No.: PCT/US2014/021919
§ 371 (c)(1),
(2) Date: Sep. 8, 2015

(87) PCT Pub. No.: WO2014/138628
PCT Pub. Date: Sep. 12, 2014

(65) Prior Publication Data
US 2016/0022862 A1    Jan. 28, 2016

Related U.S. Application Data

(60) Provisional application No. 61/774,244, filed on Mar. 7, 2013.

(51) Int. Cl.
*A61L 24/04* (2006.01)
*A61L 24/00* (2006.01)

(52) U.S. Cl.
CPC ........ *A61L 24/046* (2013.01); *A61L 24/0031* (2013.01); *A61L 24/0042* (2013.01)

(58) Field of Classification Search
CPC . A61L 24/046; A61L 24/0031; A61L 24/0042
See application file for complete search history.

(56) References Cited

U.S. PATENT DOCUMENTS

| | | | |
|---|---|---|---|
| 2002/0012705 A1* | 1/2002 | Domb | A61K 9/1652 424/493 |
| 2006/0078536 A1 | 4/2006 | Kodokian | |
| 2007/0048337 A1 | 1/2007 | Arthur | |
| 2011/0008443 A1 | 1/2011 | Alsberg et al. | |

OTHER PUBLICATIONS

Wang New Carbohydrate Mat. JACS 1992 p. 378.*

* cited by examiner

*Primary Examiner* — David J Blanchard
*Assistant Examiner* — Thurman Wheeler
(74) *Attorney, Agent, or Firm* — Tarolli, Sundheim, Covell & Tummino LLP

(57) ABSTRACT

A bioadhesive includes a crosslinked biodegradable hydrogel that includes a plurality of oxidized, acrylated or methacrylated, natural polymer. Bioadhesives are natural or synthetic materials that can be used for soft tissue repair to create a seal preventing leakage of biological fluids or to reinforce anatomic integrity as an attractive alternative to sutures and staples. The most widely used bioadhesives are fibrin, cyanoacrylates, and albumin-glutaraldehyde bioadhesives.

24 Claims, 8 Drawing Sheets

(A)
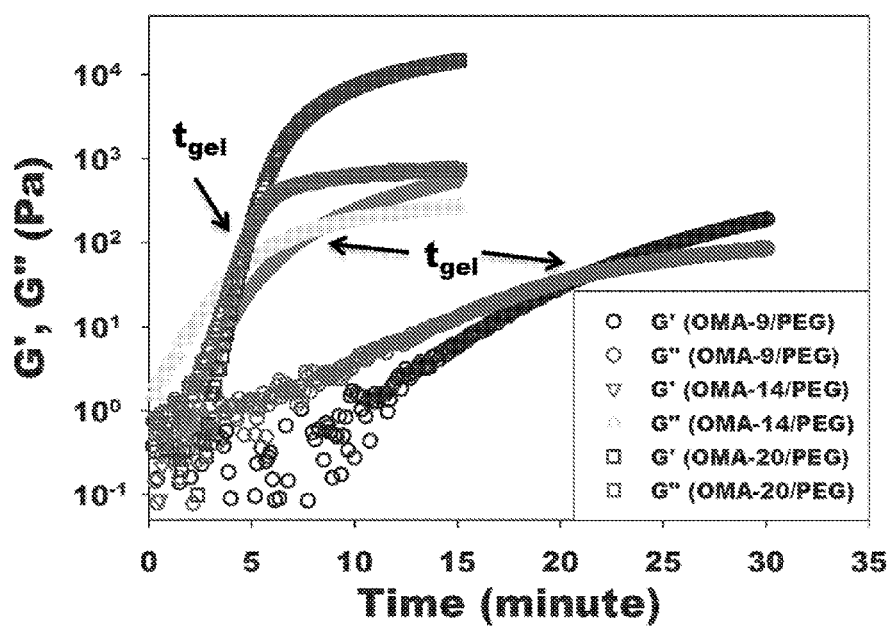
(B)
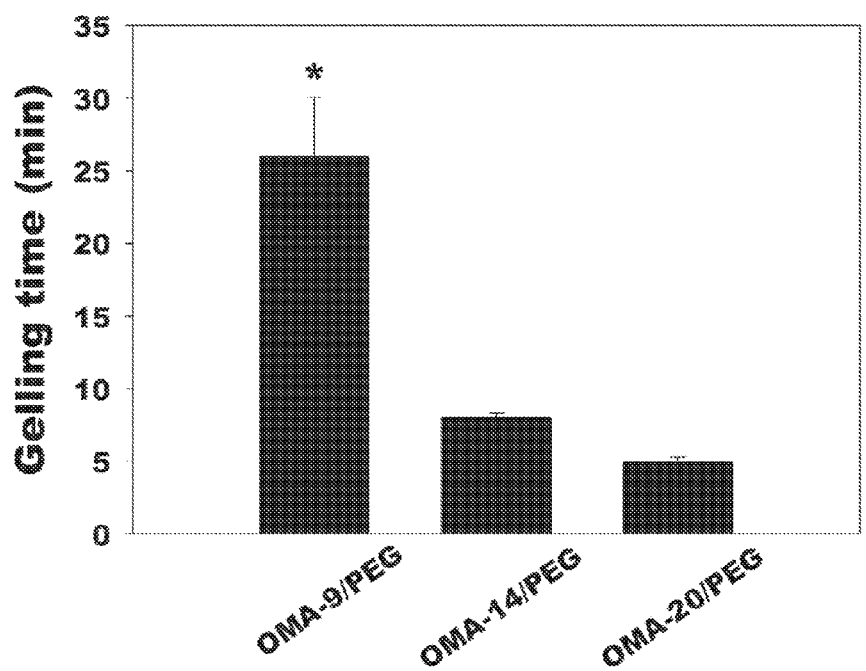
Figs. 2A-B

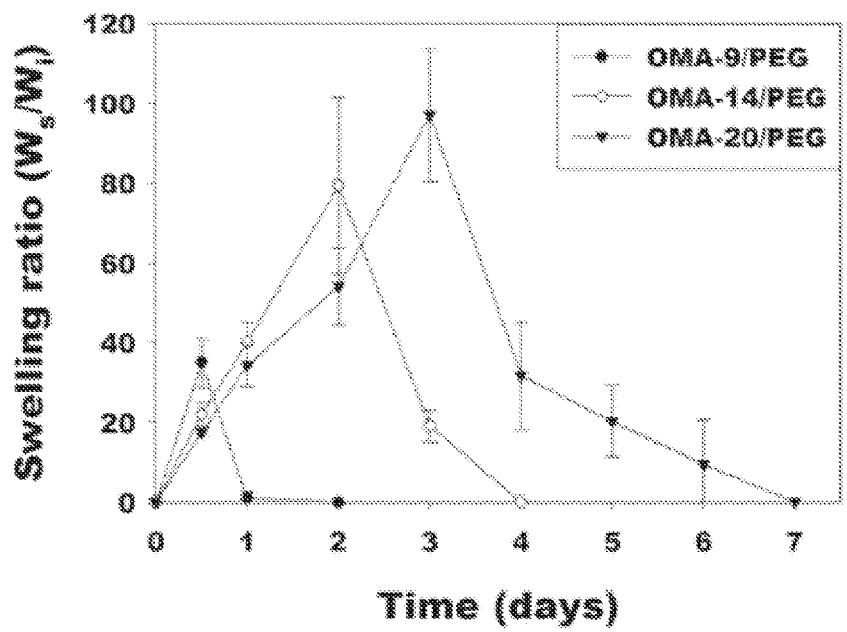
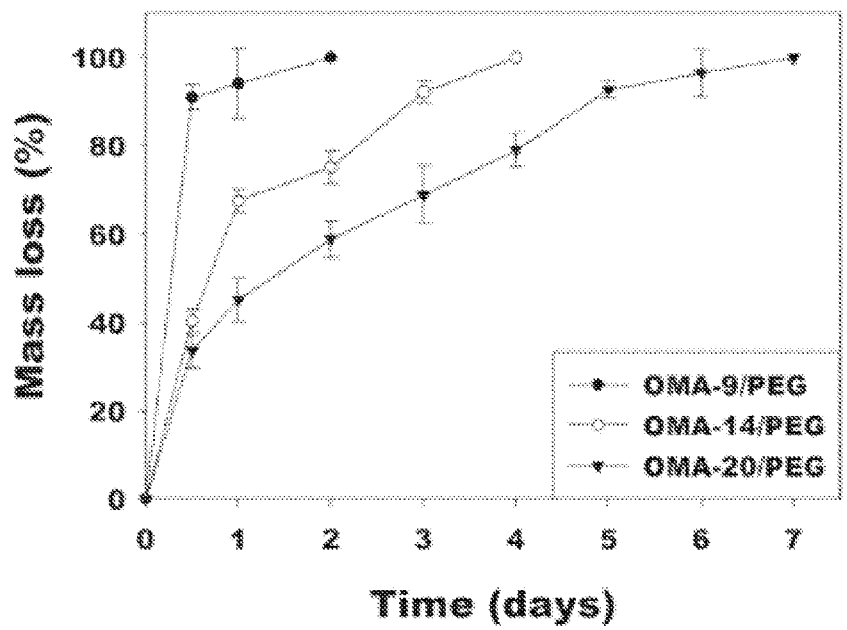
Figs. 4A-B

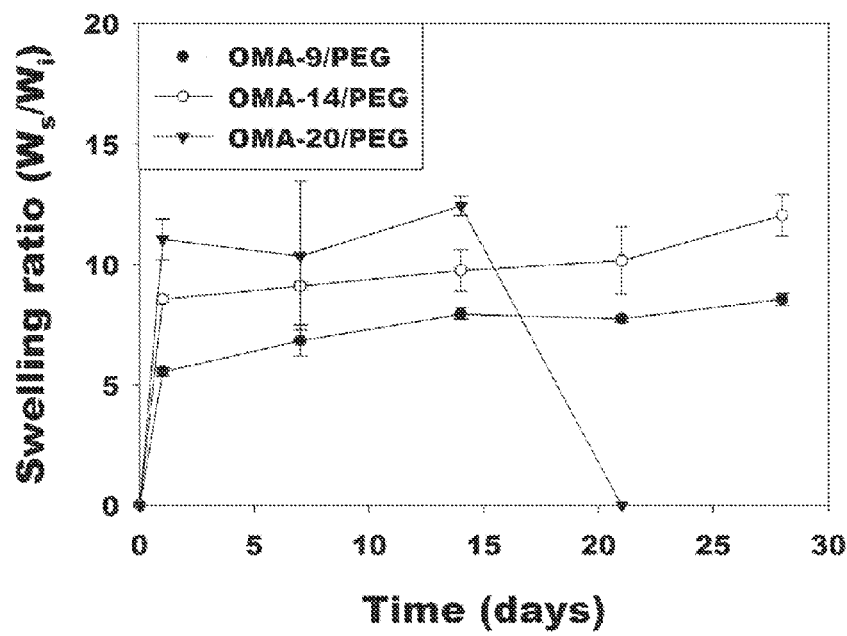
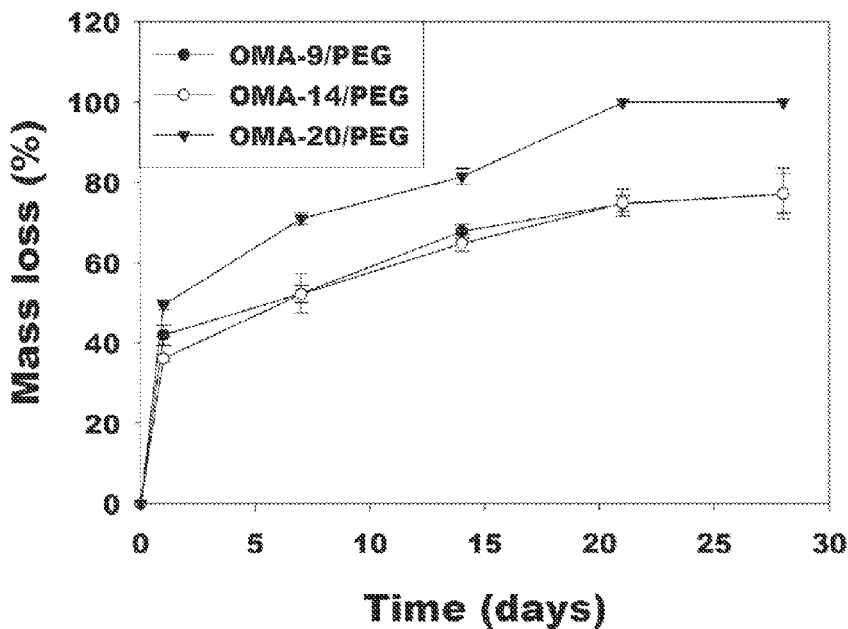
Figs. 4C-D

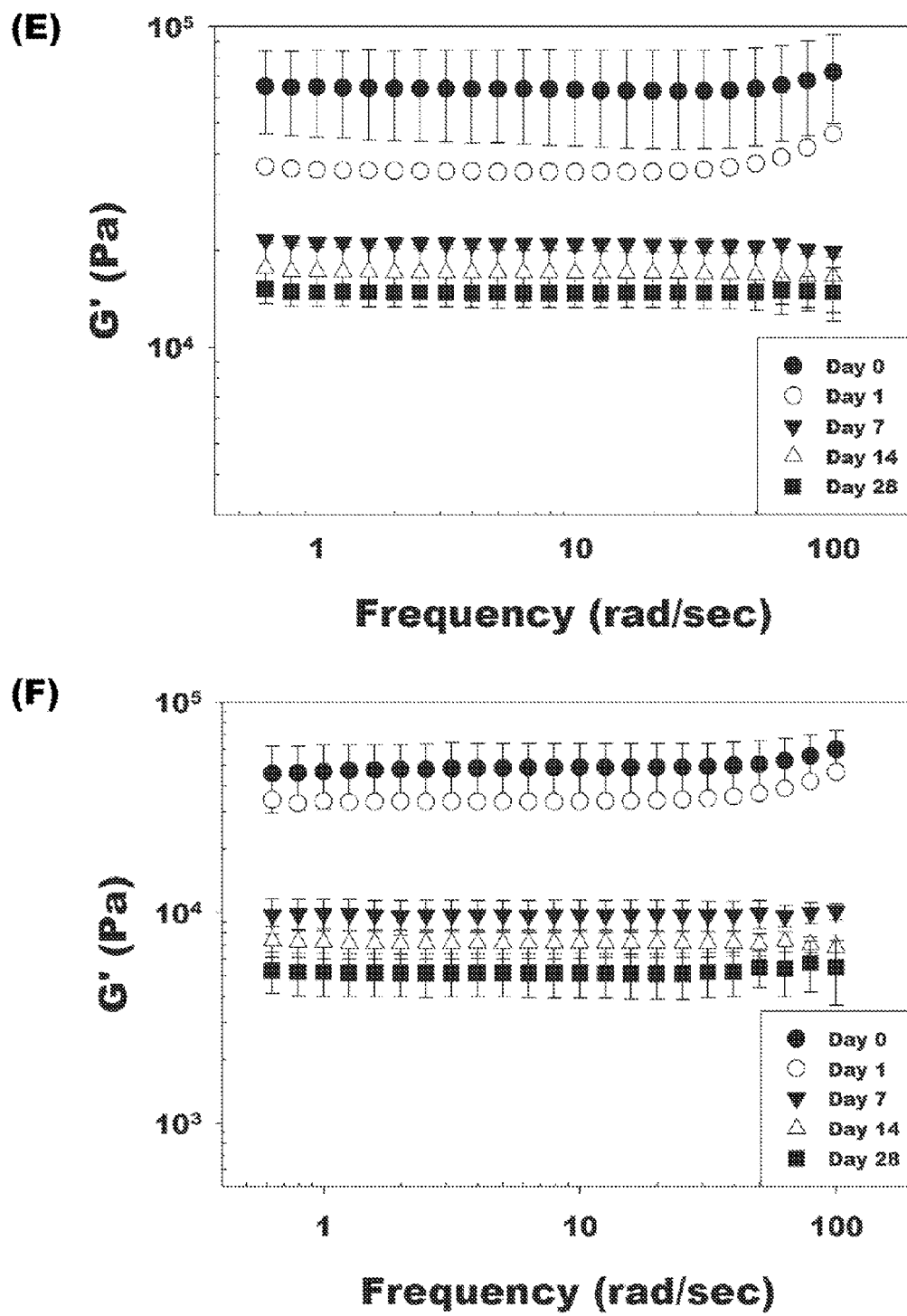
Figs. 4E-F

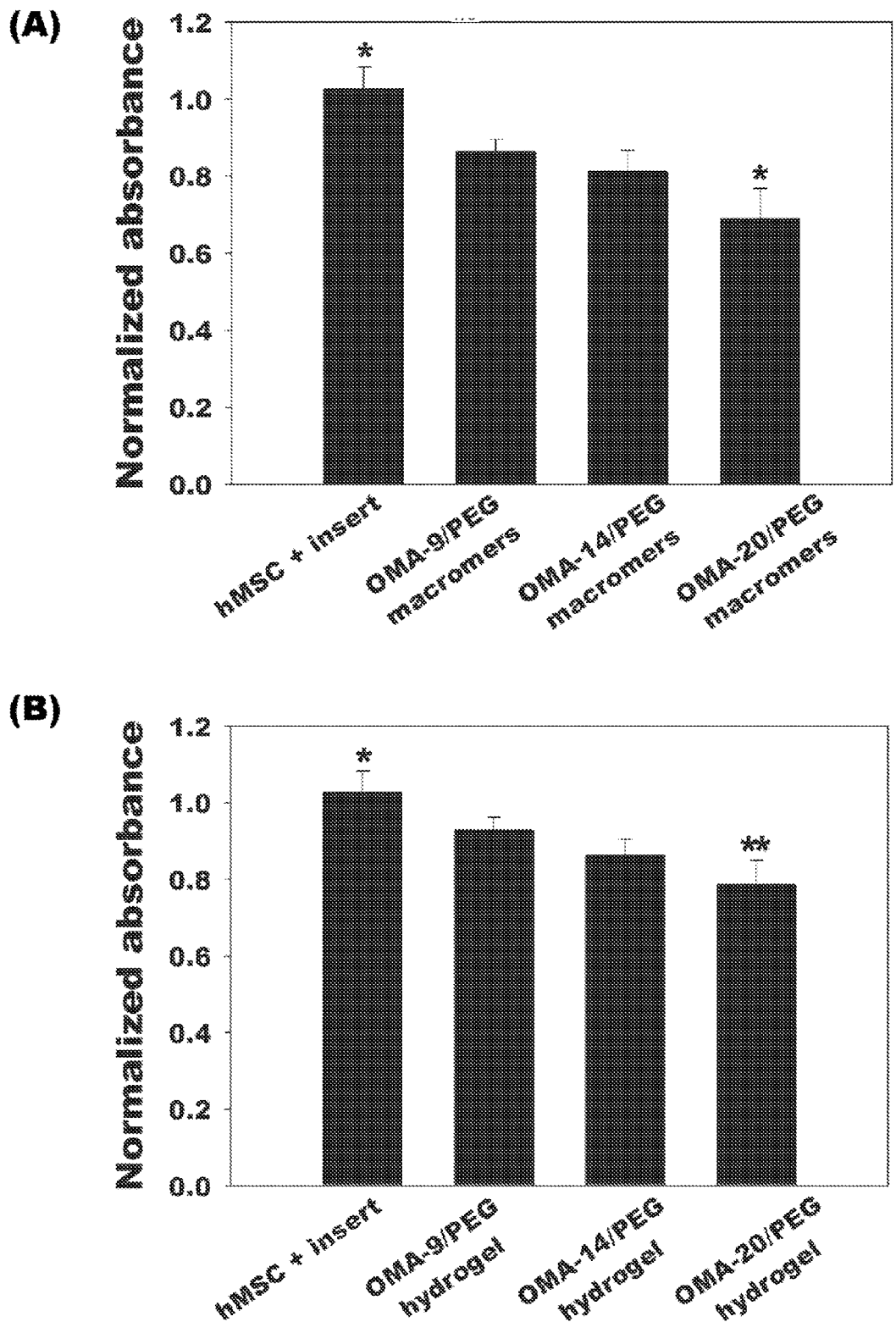
Figs. 5A-B

BIOADHESIVE HYDROGELS

RELATED APPLICATION

This application claims priority from U.S. Provisional Application No. 61/774,244, filed Mar. 7, 2013, the subject matter of which is incorporated herein by reference in its entirety.

TECHNICAL FIELD

The present invention relates to biomaterials with adhesive properties and the use thereof in biomedical applications, and particularly relates to bioadhesive hydrogels and films and uses thereof.

BACKGROUND

Bioadhesives are natural or synthetic materials that can be used for soft tissue repair to create a seal preventing leakage of biological fluids or to reinforce anatomic integrity as an attractive alternative to sutures and staples. The most widely used bioadhesives are fibrin, cyanoacrylates, and albumin-glutaraldehyde bioadhesives. Fibrin bioadhesive, which is formed by mixing fibrinogen and thrombin and commercially available as Tisseel (Baxter, Westlake Village, Calif.) and Hemaseel (Hemacure, Sarasota, Fla.), is the most widely used surgical bioadhesive in clinical practice because it is biodegradable and biocompatible. However, fibrin bioadhesive exhibits relatively weak adhesion to tissues and fast degradation compared to cyanoacrylate and albumin-glutaraldehyde bioadhesives. In addition, there is the risk of viral disease transmission, since fibrinogen is obtained from human plasma. Cyanoacrylate (Dermabond, Ethicon Inc., Somerville, N.J.) is a synthetic bioadhesive that polymerizes in the presence of body fluids. Although cyanoacrylates have performed satisfactorily in many clinical applications, they form solid impermeable polymers which release formaldehyde that can cause an inflammatory response and local tissue necrosis. Albumin-glutaraldehyde bioadhesive (BioGlue, CryoLife Europa, Hampshire, United Kingdom) has also been used in surgical procedures after it was shown to aid in achieving hemostasis around sutures or staples in large blood vessels. Although albumin-glutaraldehyde bioadhesive exhibits strong adhesion strength to tissues and biomaterials, it can cause significant problems in vivo, such as edema, an inflammatory response, and tissue necrosis.

SUMMARY

Embodiments described herein relate to biodegradable, cytocompatible bioadhesives that can be used in biomedical applications, such as drug delivery, wound closure and healing, tissue repair, biomedical device implantation, and tissue engineering. The bioadhesive comprises a crosslinked biodegradable hydrogel that includes a plurality of oxidized, acrylated or methacrylated, natural polymer macromers crosslinked with a plurality of branched poly(ethylene glycol) macromers. The degree of oxidation of the oxidized, acrylated or methacrylated, natural polymer macromers and crosslinking of the hydrogel can be controlled or varied to provide the hydrogel with controllable mechanical properties, adhesion strength, and biodegradation rate. The hydrogel can, upon degradation, for example, in in vivo applications, produce substantially non-toxic products.

In some embodiments, the oxidized, acrylated or methacrylated, natural polymer macromers are polysaccharides, which are oxidized so that about 1% to about 50% of the saccharide units therein are converted to aldehyde saccharide units. For example, the oxidized, acrylated or methacrylated, natural polymer macromers can include oxidized, acrylated or methacrylated, alginates, which are oxidized so that about 1% to about 50% of the saccharide units therein are converted to aldehyde saccharide units.

In other embodiments, acrylate or methacrylate groups of the natural polymer macromers are crosslinked so that the hydrogel is dual-crosslinked. The acrylate or methacrylate groups can be photocrosslinked by contacting the hydrogel with a photoinitiator and exposing the hydrogel to a light source to initiate crosslinking of the acrylate or methacrylate groups. The acrylate or methacrylate groups can form a plurality of hydrolyzable crosslinks that are degradable in vivo.

In some embodiments, the poly(ethylene glycol) macromers are poly(ethylene glycol) amine macromers, such as n-arm poly(ethylene glycol) amines, where n is an integer greater than 1. The amine groups of the poly(ethylene glycol) amine macromers can react with aldehyde groups of the natural polymer macromers to crosslink the hydrogel.

Other embodiments, described herein relate to a method of preparing a bioadhesive. The method includes reacting a plurality of oxidized, acrylated or methacrylated, natural polymer macromers with a plurality of branched poly(ethylene glycol) macromers to form a hydrogel, wherein the plurality of branched poly(ethylene glycol) macromers crosslink the plurality of oxidized, acrylated or methacrylated, natural polymer macromers. The acrylate or methacrylate groups of the oxidized, acrylated or methacrylated, natural polymer macromers can then be cross-linked so the hydrogel is dual crosslinked.

In some embodiments, the oxidized, acrylated or methacrylated, natural polymer macromers are polysaccharides, which are oxidized so that about 1% to about 50% of the saccharide units therein are converted to aldehyde saccharide units. For example, the oxidized, acrylated or methacrylated, natural polymer macromers can include oxidized, acrylated or methacrylated, alginates, which are oxidized so that about 1% to about 50% of the saccharide units therein are converted to aldehyde saccharide units.

In other embodiments, the acrylate or methacrylate groups can be photocrosslinked by contacting the hydrogel with a photoinitiator and exposing the hydrogel to a light source to initiate crosslinking of the acrylate or methacrylate groups. The acrylate or methacrylate groups can form a plurality of hydrolyzable crosslinks that are degradable in vivo.

In some embodiments, the poly(ethylene glycol) macromers are poly(ethylene glycol) amine macromers, such as n-arm poly(ethylene glycol) amines, where n is an integer greater than 1. The amine groups of the poly(ethylene glycol) amine macromers can react with aldehyde groups of the acrylate or methacrylate groups of the natural polymer macromers to crosslink the hydrogel.

BRIEF DESCRIPTION OF THE DRAWINGS

FIG. 2(A-B) illustrate: (A) a plot showing representative storage moduli (G') and loss moduli (G") over time; and (B) a graph showing quantification of gelling time for the single-crosslinked OMA/PEG hydrogels at 25° C. The time where G' and G" crossover occurred is denoted $t_{gel}$ (gelling point). Values represent mean±standard deviation (N=3). *p<0.05 compared with the other groups.

FIG. 4(A-F) illustrate plots showing the swelling ratios and mass loss of the single-crosslinked OMA/PEG hydrogels [(A) and (B), respectively] and the dual-crosslinked OMA/PEG hydrogels [(C) and (D), respectively] in DMEM over time. Storage modulus (G') changes of the dual-crosslinked (E) OMA-9/PEG and (F) OMA-14/PEG hydrogels in DMEM over time. Values represent mean±standard deviation (N=3).

FIG. 5(A-B) illustrate cytotoxicity of (A) the OMA/PEG macromers and (B) the dual-crosslinked OMA/PEG hydrogels on hMSCs after 48 hrs as quantified by MTS assay. The absorbance of experimental groups at 490 nm were normalized to that of a control group without any macromer, hydrogel material or insert in the medium. Values represent mean±standard deviation (N=5). *p<0.05 compared with the other groups. **p<0.05 compared with hMSC+insert and OMA-9/PEG hydrogel.

DETAILED DESCRIPTION

Figure 1:
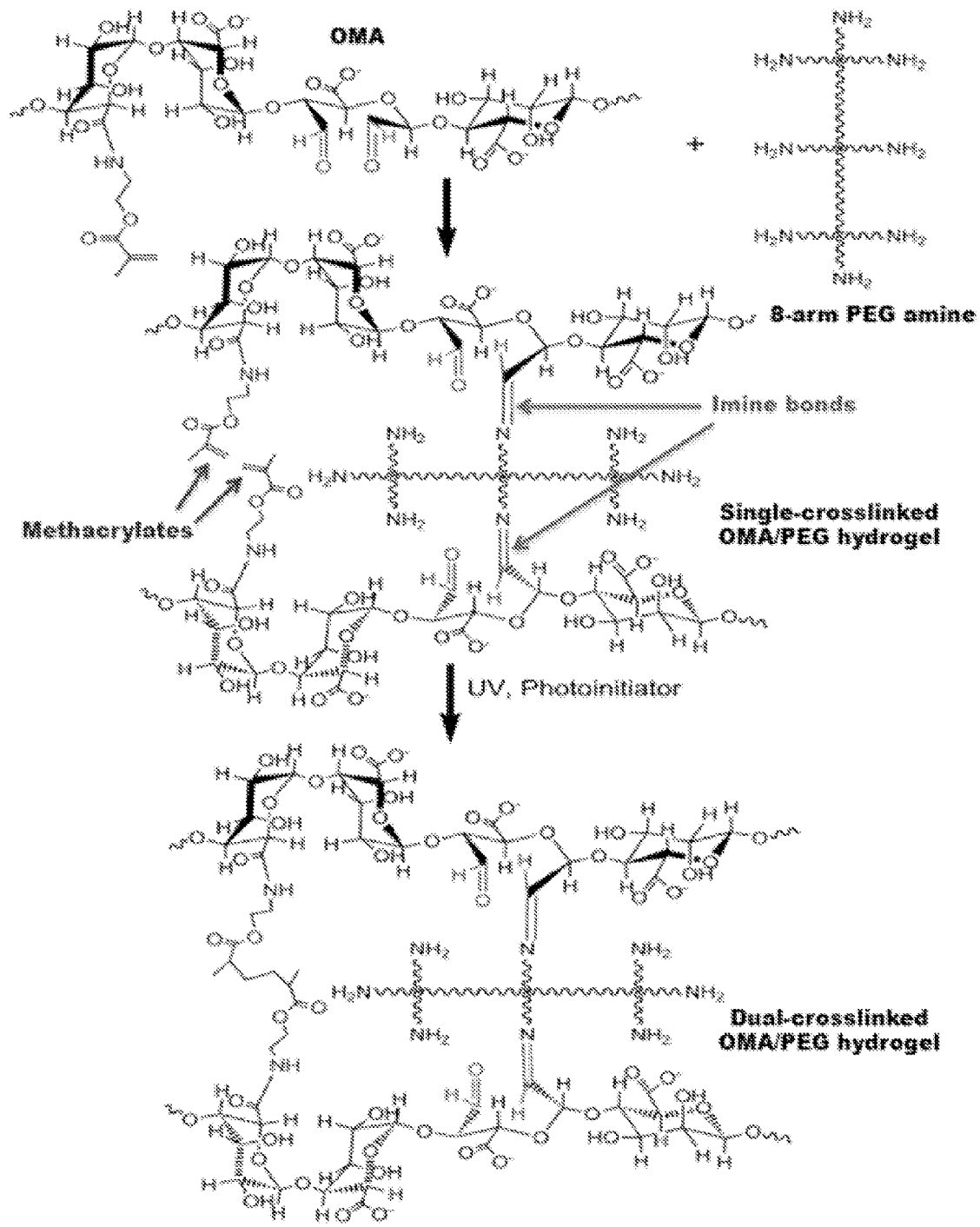
FIG. 1 is a schematic illustration of a reaction scheme for the preparation of single- and dual-crosslinked OMA/PEG hydrogels.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

The term "bioadhesive" refers to a substantially non-toxic biocompatible substance having adhesive properties, which is capable of adhering to mammalian tissue.

The term "biomaterial" refers to any naturally occurring, naturally derived, or synthetic material or substance which is compatible with biological systems.

The terms "biodegradable" and "bioresorbable" may be used interchangeably and refer to the ability of a material (e.g., a natural polymer or macromer) to be fully resorbed in vivo. "Full" can mean that no significant extracellular fragments remain. The resorption process can involve elimination of the original implant material(s) through the action of body fluids, enzymes, cells, and the like.

The term "gel" includes gels and hydrogels.

The term "macromer" can refer to any natural polymer or oligomer.

The term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

The term "tissue" can refer to an aggregate of cells having substantially the same function and/or form in a multicellular organism. "Tissue" is typically an aggregate of cells of the same origin, but may be an aggregate of cells of different origins. The cells can have the substantially same or substantially different function, and may be of the same or different type. "Tissue" can include, but is not limited to, an organ, a part of an organ, bone, cartilage, skin, neuron, axon, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic, or ascite tissue.

Embodiments described herein relate to biodegradable, cytocompatible bioadhesives that can be used in biomedical applications, such as drug delivery, wound closure and healing, tissue repair, biomedical device implantation, and tissue engineering. The bioadhesive comprises a crosslinked biodegradable hydrogel that includes a plurality of oxidized, acrylated or methacrylated, natural polymer macromers crosslinked with a plurality of branched poly(ethylene glycol) macromers. It was found that the crosslinked biodegradable hydrogel exhibited cytocompatibility when cultured with human cells, such as human mesenechymal stem cells, and had adhesion strength, measured using a porcine skin model, superior to commercially available fibrin glue. The degree of oxidation of the oxidized, acrylated or methacrylated, natural polymer macromers and crosslinking of the hydrogel can be controlled or varied to provide the hydrogel with controllable mechanical properties, adhesion strength, and biodegradation rate. The hydrogel can, upon degradation, for example, in in vivo applications, produce substantially non-toxic products.

In some embodiments, the natural polymer macromers that are oxidized and acrylate or methacrylated can include saccharides (e.g., mono-, di-, oligo-, and poly-saccharides), such as glucose, galactose, fructose, lactose and sucrose, collagen, gelatin, glycosaminoglycans, poly(hyaluronic acid), poly(sodium alginate), hyaluronan, alginate, heparin and agarose that can be readily oxidized to form free aldehyde units.

In some embodiments, the oxidized, acrylated or methacrylated, natural polymer macromers are polysaccharides, which are oxidized so that about 1% to about 50% of the saccharide units therein are converted to aldehyde saccharide units. Control over the degree of oxidation of the natural polymer macromers permits regulation of the gelling time used to form the hydrogel as well as the bioadhesive mechanical properties, which allows for tailoring of these bioadhesive properties depending on the clinical application.

In other embodiments, oxidized, acrylated or methacrylated, natural polymer macromers can include oxidized, acrylated or methacrylated, alginates, which are oxidized so that about 1% to about 50% of the saccharide units therein are converted to aldehyde saccharide units. Natural source alginates, for example, from seaweed or bacteria, are useful and can be selected to provide side chains with appropriate M (mannuronate) and G (guluronate) units for the ultimate use of the polymer. Alginate materiala can be selected with high guluronate content since the guluronate units, as opposed to the mannuronate units, more readily provide sites for oxidation and crosslinking. Isolation of alginate chains from natural sources can be conducted by conventional methods. See Biomaterials: Novel Materials from Biological Sources, ed. Byrum, Alginates chapter (ed. Sutherland), p. 309-331 (1991). Alternatively, synthetically prepared alginates having a selected M and G unit proportion and distribution prepared by synthetic routes, such as those analogous to methods known in the art, can be used. Further, either natural or synthetic source alginates may be modified to provide M and G units with a modified structure. The M and/or G units may also be modified, for example, with polyalkylene oxide units of varied molecular weight such as shown for modification of polysaccharides in Spaltro (U.S. Pat. No. 5,490,978) with other alcohols such as glycols. Such modification generally will make the polymer more soluble, which generally will result in a less viscous material. Such modifying groups can also enhance the stability of the polymer. Further, modification to provide alkali resistance, for example, as shown by U.S. Pat. No. 2,536,893, can be conducted.

The oxidation of the natural polymer macromers (e.g., alginate material) can be performed using a periodate oxidation agent, such as sodium periodate, to provide at least some of the saccharide units of the natural polymer macromer with aldehyde groups. The degree of oxidation is controllable by the mole equivalent of oxidation agent, e.g., periodate, to saccharide unit. For example, using sodium periodate in an equivalent % of from 2% to 100%, preferably 1% to 50%, a resulting degree of oxidation, i.e., % if saccharide units converted to aldehyde saccharide units, from about 2% to 50% can be obtained. The aldehyde groups provide functional sites for crosslinking and for bonding tissue, cells, prosthetics, grafts, and other material that is desired to be adhered. Further, oxidation of the natural polymer macromer facilitates their degradation in vivo, even if they are not lowered in molecular weight. Thus, high molecular weight alginates, e.g., of up to 300,000 daltons, may be degradeable in vivo, when sufficiently oxidized, i.e., preferably at least 5% of the saccharide units are oxidized.

The oxidized natural polymer macromer (e.g., alginate) can be acrylated or methacrylated by reacting an acryl group or methacryl with a natural polymer or oligomer to form the oxidized, acrylated or methacrylated natural polymer macromer (e.g., alginate). For example, oxidized alginate can be dissolved in a solution chemically functionalized with N-hydroxysuccinimide and 1-ethyl-3-(3-dimethylaminopropyl)-carbodiimide hydrochloride to activate the carboxylic acids of alginate and then reacted with 2-amionethylmethacrylate to provide a plurality of methacrylate groups on the alginate.

The degree of acrylation or methacrylation can be controlled to control the degree of subsequent crosslinking of the acrylate and methacrylates as well as the mechanical properties, adhesion strength, and biodegradation rate of the bioadhesive. The degree of acrylation or methacrylation can be about 1% to about 50%, although this ratio can vary more or less depending on the end use of the bioadhesive.

The oxidized, acyrlated or methacrylated natural polymer macromer can be cross-linked with a plurality of poly (ethylene glycol) macromers to form the crosslinked biodegradable hydrogel. The poly(ethylene glycol) macromers can have an average molecular weight of about 1,000 to about 50,000 Daltons.

In some embodiments, the poly(ethylene glycol) macromer can be a branched poly(ethylene glycol) macromer that includes a plurality of functional groups that bind to or react with the aldehyde groups of the oxidized, acrylated or methacrylated natural polymer macromer to crosslink the natural polymer macromer. Examples of branched poly (ethylene glycol) macromers that can be used to crosslink the oxidized, acrylated or methacrylated natural polymer macromer can include n-arm-poly(ethylene glycol) amines (n-arm-PEG-NH), n-arm-poly(ethylene glycol)-acrylate (n-arm-PEG-A), n-arm-poly(ethylene glycol)-thiol (n-arm-PEG-SH), n-arm-poly(ethylene glycol)-azide (n-arm-PEG-azide), and n-arm-poly(ethylene glycol)-alkyne (n-arm-PEG-alkyne), where n is an integer greater than 1 (e.g., n=2, 3, 4, 5, 6, 7, 8, 10, etc.)

In some embodiments, the branched poly(ethylene glycol) macromer can be an n-arm-poly(ethylene glycol) amines (n-arm-PEG-NH), with an average moleclular weight of about 5,000 to about 20,000 daltons. The n-arm-PEG-NH when reacted with the oxidized, acrylated or methacrylated natural polymer macromer can form first crosslinking networks by Schiff base reaction between aldehyde groups of the oxidized, acrylated or methacrylated natural polymer macromer and amines of the n-arm-PEG-NH and provide the cohesive force that stabilizes the bioadhesive into a hydrogel.

The extent of crosslinking can be controlled by the concentration of poly(ethylene glycol) macromer and the degree of oxidation of the oxidized, acrylated or methacrylated natural polymer macromer. The higher concentration or degree of either corresponding to a higher extent of crosslinking. The extent of crosslinking alters the mechanical properties of the gel and can be controlled as desired for the particular application. In general, a higher degree of crosslinking results in a stiffer gel having a lower degradation rate.

In some embodiments, a plurality of second crosslink networks can be formed by crosslinking acrylate or methacrylate groups of the oxidized, acrylated or methacrylated natural polymer macromer. The second crosslinking networks formed by crosslinking the acrylate groups or methacrylate groups of the oxidized, acrylated or methacrylated natural polymer macromer can provide improved mechanical properties, such as resistance to shear or tensile loading and excessive swelling, as well as delayed biodegradation rate of the bioadhesive so formed. For example, the storage modulus of the hydrogels was strongly enhanced by secondary crosslinking. Since bioadhesives may be exposed to mechanical forces (i.e., shear and tensile force) in in vivo environments, the increased mechanical properties of the hydrogels following secondary crosslinking may contribute to improving their stability when used in such applications.

The swelling behavior, mechanical properties, and degradation rates of the hydrogel can be controlled by changing the percentage of crosslinks in the hydrogel. The percentage of crosslinks can be varied between about 1% and about 50% by weight, and, for example, between about 4% and about 25% by weight.

In some embodiments, the acrylate or methacrylate groups of the oxidized, acrylated or methacrylated natural polymer macromer of the hydrogel can be crosslinked by photocrosslinking using UV light in the presence of photoinitiators. For example, oxidized, acrylated or methacrylated natural polymer macromers of the hydrogel can be photocrosslinked in an appropriate amount of $diH_2O$ or aqueous media (e.g., PBS) containing a desired amount of a photoinitiator.

The solution can then be injected into a curing vessel and exposed to a light source at a wavelength and for a time to promote cross-linking of the acrylate groups of the polymers and form the photocrosslinked biodegradable hydrogel. For example, the polymers can be exposed to UV light of about 320-500 nm at about 3.5 mW $cm^{-2}$ for about 85 seconds using an Omnicure 51000 UV Spot Cure System (Lumen Dynamics Group, Mississauga, Ontario, Canada) to form the hydrogel.

A photoinitiator can include any photo-initiator that can initiate or induce polymerization of the acrylate or methacrylate macromer. Examples of the photoinitiator can include camphorquinone, benzoin methyl ether, 2-hydroxy-2-methyl-1-phenyl-1-propanone, diphenyl(2,4,6-trimethyl-benzoyl)phosphine oxide, benzoin ethyl ether, benzophenone, 9,10-anthraquinone, ethyl-4-N,N-dimethylaminobenzoate, diphenyliodonium chloride and derivatives thereof.

In some embodiments, the acrylate or methacrylate crosslinks can be readily hydrolyzed in vivo to promote degradation of the hydrogel. In one example, the hydrolyzable crosslink can include at least one hydrolyzable acrylate (e.g., methacrylate) cross-link. The hydrolyzable acrylate cross-link can include at least one hydrolyzable ester and/or hydrolyzable amide linkage. As explained further below, hydrolytic degradation of the hydrolyzable acrylate cross-link can create space for cell growth and tissue repair to replace the bioadhesive in vivo.

In some embodiments, the bioadhesive may further comprise an agent, which increases film tensile strength and/or adhesion. For example, the bioadhesive may include one or more agents which are capable of increasing the amount of hydrogen bonding between the hydrogel and tissue of the subject, and/or may increase the electrostatic interaction between the hydrogel and tissue; and/or may increase mechanical bonding between the hydrogel and tissue.

The single-crosslinked or dual-crosslinked bioadhesive hydrogel can be used in a variety of biomedical applications, including tissue engineering, drug discovery applications, and regenerative medicine. The bioadhesive may be used separately, or in combination, to achieve mechanical closure of tears, holes, incisions, etc, in tissue. The bioadhesive may also be used to strengthen tissue or form a seal over a tear, hole, incision, leak etc. In some embodiments, the bioadhesive may be useful for mechanically joining and/or sealing a tissue site and, for example, may reduce or prevent fluid and/or gas release or diffusion from a tissue site.

The bioadhesives described herein can have tensile strength and flexibility such that they may be suitable for use in tissue repair. For example, the bioadhesive can be provided as a bioadhesive film or hydrogel that has a degree of flexibility, which allows the films to be manipulated, e.g., bent, twisted, or stretched, without substantial breakage. In some embodiments, bioadhesive films and gels according can have adhesive strength greater than about 20 kPa. The adhesive strength may be greater than about 5, 10, 15, 20, 25 or 30 kPa, and may be about 5, 10, 15, 20, 25 or 30 or more than 30 kPa. Bioadhesive films and gels according to the present invention may be used as sealants and suitably may have a burst pressure >about 40 mmHg. The burst pressure may be greater than about 20 mmHg, or greater than about 25, 30, 35, 40, 45, 50, 55 or 60 mmHg, and may be about 20, 25, 30, 35, 40, 45, 50, 55, 60 or more than 60 mmHg.

In some embodiments, the bioadhesive described herein can be used to repair tissue defects, such as torn, herniated, or otherwise damaged tissue. The tissue can vary in nature but includes cardiovascular, vascular, epithelial, ligament, tendon, muscle, bone and the like. In some embodiments, the tissue defect can include a defect caused by the destruction of bone or cartilage. For example, one type of cartilage defect can include a joint surface defect. Joint surface defects can be the result of a physical injury to one or more joints or, alternatively, a result of genetic or environmental factors. Most frequently, but not exclusively, such a defect will occur in the knee and will be caused by trauma, ligamentous instability, malalignment of the extremity, meniscectomy, failed aci or mosaicplasty procedures, primary osteochondritis dessecans, osteoarthritis (early osteoarthritis or unicompartimental osteochondral defects), or tissue removal (e.g., due to cancer). Examples of bone defects can include any structural and/or functional skeletal abnormalities. Non-limiting examples of bone defects can include those associated with vertebral body or disc injury/destruction, spinal fusion, injured meniscus, avascular necrosis, cranio-facial repair/reconstruction (including dental repair/reconstruction), osteoarthritis, osteosclerosis, osteoporosis, implant fixation, trauma, and other inheritable or acquired bone disorders and diseases.

The bioadhesive can also be utilized with general surgical techniques or with more advanced laparoscopic techniques to adhere engineered or natural tissue grafts or constructs. Once the bioadhesive is applied to the damaged/injured site, engineered or natural tissue grafts or contsructs can be directly adhered to the tissue. Alternatively and in addition to the adherence of the bioadhesive to the tissue, staples, sutures or tacks and the like can also be used to help secure the engineered or natural tissue grafts or constructs.

In addition to tendon and ligament repair and hernia repair, the bioadhesive can potentially be utilized in cardiovascular surgery to attach prosthetic vascular grafts. Over 600,000 vascular grafts are implanted annually to replace damaged blood vessels. Coronary artery bypass grafting (CABG) is the most common method of replacing diseased blood vessels. When no suitable autologous vessels are available, there are several synthetic materials used for prosthetic vascular grafts such as PTFE, polyurethane and Dacron. Regardless of the graft material used, the bioadhesive described herein can be used to secure the graft to the existing tissue.

In other embodiments, the bioadhesive can be used to secure dental implants. Collagen membranes have been utilized in guided bone regeneration (GBR) to promote implant wound healing in clinical periodontics. Materials used in GBR are either placed over the defect followed by wound closure, or can be sutured in place prior to wound closure. Bioadhesive described herein could reduce surgery time and simplify the process of securing the membrane.

In still other embodiments, the bioadhesive can be used to repair the entrance portal in annulus fibrosis used for insertion of nucleus fibrosis replacement; prevent extrusion of implant by patch fixation. The bioadhesive can also be used for the repair of annulus fibrosis in herniated disc or after discectomy by patch fixation.

The bioadhesive can also be used secure bone graft, treat stress fractures, as well as repair lesions in avascular portion of knee meniscus. The bioadhesive can be used to stabilize a meniscal tear and connect the avascular region with vascular periphery to encourage ingrowth of vascularity and recruitment of meniscal progenitor cells. Current techniques lead to repair with weak non-meniscal fibrous scar tissue. The bioadhesive may also serve as vehicle for delivery of growth factors and progenitor cells to enhance meniscus repair.

In some embodiments, the bioadhesive described herein may be used for repairing a discontinuity in an area of tissue. A discontinuity in this context may be for example a tear, hole, incision, leak, cut, a lesion, a graze, a cavity or some other type of discontinuity. The bioadhesive may be applied to the tissue such that said area of tissue to be repaired is partially or fully covered by one or more films of the bioadhesive. The films may at least partially overlap, or may be layered, or may not overlap, in order to increase either the area of repair, or the strength of the repair, or both.

A method for repairing a discontinuity in an area of tissue may therefore comprise applying a bioadhesive hydrogel described herein to an area of tissue near the site to be repaired such that the area of tissue to be repaired is partially or fully covered by the gel. In some embodiments, where the hydrogel is crosslinked a photocrosslinker. Light sufficient to crosslink the hydrogel can be applied before or after application of bioadhesive to the area of the tissue to be repaired.

For example, the repair may be effected by applying a bioadhesive hydrogel to the tissue such that said area of tissue to be repaired is partially or fully covered by the hydrogel. The hydrogel may be then irradiated or illuminated with UV light from a light source. The irradiation or illumination of the gel may then further crosslink the gel.

In some embodiments, a wound healing agent may be used in conjunction with a bioadhesive. The wound healing agent may be applied to at least part of a wound, e.g., the tissue to be repaired or to the parts to be joined. The bioadhesive may then be applied over the wound healing agent so that it contacts a part of the tissue and covers the wound healing agent. The wound healing agent may be any of the wound healing agents known in the art.

Bioadhesives described herein, including compositions in the form of bioadhesive films or hydrogels, may also function as drug delivery systems to deliver therapeutic agent(s) to a tissue repair site. For example, a bioadhesive film may be attached to a drug delivery medium. The film, gel, or both, may comprise one or more therapeutic agents or other additives. Examples of therapeutic agents include antibiotics; antifungal agents; nucleic acids (e.g., RNA, DNA, including cDNA); proteins, including proteins within a delivery vehicle such as a liposome, or virus; enzymes; enzyme inhibitors; growth factors, haemostatic agents, anti-inflammatory agents, anaesthetics; thrombolytics; thrombogenics, etc. The therapeutic agent may be added to the bioadhesive film and/or gel prior to application to tissue. Alternatively, the therapeutic agent may coat or partially coat one or more surfaces of the bioadhesive film and/or gel. Bioadhesives described herein may also be used concurrently with other therapies or therapeutic regimes to reduce the risk of infection and/or to promote healing.

EXAMPLE

In this Example, we engineered a dual-crosslinked oxidized, methacrylated alginate/8-arm poly(ethylene glycol) amine (OMA/PEG) hydrogel system as a bioadhesive with controllable mechanical properties, adhesion strength and biodegradation rate. Alginate was chemically functionalized with aldehyde groups by oxidation to react with amine groups of PEG, and with 2-aminoethylmethacrylate (AEMA) via carbodiimide chemistry to allow photocrosslinking of the methacrylate groups by ultraviolet (UV) light. The effect of varying the degree of alginate oxidation was evaluated through examination of hydrogel shear moduli, swelling behavior, degradation profiles and adhesion strength with porcine skin. The OMA/PEG hydrogel system exhibits cytocompatibility and controllable physical properties. The bioadhesion strength of this system is tunable by varying the alginate oxidation level and superior to commercially available fibrin glue as measured using porcine skin. This dual-crosslinked OMA/PEG bioadhesive hydrogel system with controllable physical properties and bioadhesion strength is useful for a wide range of clinical applications.

Materials and Methods

Preparation of OMA and 8-Arm PEG-Amine

The OMA macromers were prepared as follows. Briefly, to prepare the oxidized alginate, sodium alginate (20 g, Protanal LF 20/40, 196,000 g/mol, FMC Biopolymer, Philadelphia, Pa.) was dissolved in ultrapure deionized water ($diH_2O$, 1800 ml). Sodium periodate (2, 3.5 and 5 g, Sigma, St. Louis, Mo.) was dissolved in 200 ml $diH_2O$ and added into separate alginate solutions to achieve different degrees of theoretical alginate oxidation (10, 17.5, and 25%) under stirring in the dark at room temperature. The oxidation was stopped after 24 hrs by addition of ethylene glycol (molar ratio of ethylene glycol:sodium periodate=1:1, Sigma). The oxidized alginate was purified by dialysis (MWCO=3500, Spectrum Laboratories Inc., Rancho Dominguez, Calif.) against $diH_2O$ for 3 days, filtered (0.22 μm filter, Fisher Scientific, Pittsburgh, Pa.), and lyophilized. To prepare OMAs at theoretical methacrylation of 45%, oxidized alginate (10 g) was dissolved in 50 mM 2-morpholinoethanesulfonic acid (Sigma) buffer solution (1000 ml, pH 6.5) containing 0.5 M NaCl (Fisher). N-hydroxysuccinimide (2.65 g, Sigma) and 1-ethyl-3-(3-dimethylaminopropyl)-carbodiimide hydrochloride (8.75 g, Sigma) were added to the mixture to activate the carboxylic acids of alginate. After 5 min, AEMA (3.8 g, Polysciences, Warrington, Pa.) was added to the solution, and the reaction was maintained in the dark at room temperature for 24 hrs. The reaction mixture was precipitated with the addition of excess acetone, dried in a chemical fume hood, and rehydrated to a 1% solution in $diH_2O$ for further purification. The OMA was purified by dialysis (MWCO=3500, Spectrum Laboratories Inc.) against $diH_2O$ for 3 days, treated with activated charcoal (5 g/1000 ml, 50-200 mesh, Fisher) for 30 min, filtered (0.22 μm filter) and lyophilized. The OMA was dissolved in deuterium oxide ($D_2O$, 2 w/v %), and placed in a NMR tube. To analyze the oxidation and methacrylation efficiency of the OMAs, $^1$H-NMR spectra were recorded on a Varian Unity-300 (300 MHz) NMR spectrometer (Varian Inc., Palo Alto, Calif., USA) using 3-(trimethylsilyl)propionic acid-$d_4$ sodium salt (0.05 w/v %) as an internal standard. The actual degrees of oxidation and methacrylation were calculated from $^1$H-NMR spectra as previously reported. The actual degree of oxidation of the alginates, which was used in a naming code for the different formulations (OMA-9, OMA-14, and OMA-20), was 9%, 14%, and 20%. The actual degree of methacrylation of OMA-9, OMA-14 and OMA-20 was 19%, 21% and 25%, respectively. Eight-arm poly(ethylene glycol)-amine hydrochloric acid salt (PEG/HCl, 20 g, Mw=10,000 Da, Jenkem Technology USA Inc., Allen, Tex.) was dissolved in 100 ml methylene chloride, and triethylamine (the mole ratio of triethylamine to HCl of PEG/HCl=2) was added into the PEG solution in order to remove HCl salt from the PEG/HCl. After 24 hrs, the solution was precipitated into an excess of hexanes (Fisher), dried in a chemical fume hood, and rehydrated to a 10% (w/v) solution in diH$_2$O for further purification. The PEG was purified by dialysis (MWCO 3500; Spectrum Laboratories Inc.) against diH$_2$O for 3 days, filtered (0.22 μm filter) and lyophilized.

Determination of Gelling Time of the Single-Crosslinked OMA/PEG Hydrogels

To examine gelling properties of the OMA/PEG hydrogels, dynamic rheological measurements were performed with a strain-controlled rheometer (AR-2000ex; TA Instruments, New Castle, Del., USA) using a stainless steel cone and plate geometry with 4° cone angle and 20 mm cone diameter. Plate temperature was maintained at 25° C. OMA (20 w/v %) and PEG (40 w/v %) were separately dissolved in Dulbecco's Modified Eagle Medium with low glucose (DMEM, Sigma) with 0.05% w/v photoinitiator (Irgacure-2959, Sigma). One 1 ml syringe containing 250 μl of OMA solution was joined with a Luer-Lok connector to another 1 ml syringe containing an equal volume of PEG solution, and the two solutions were mixed for 30 s. Immediately after mixing, samples were deposited onto the bottom plate of the rheometer. Both the shear storage (G') and loss (G") moduli were measured every 6.5 seconds. These measurements were taken at a loading frequency of 1 Hz and strain of 0.2%. Each measurement was performed three times. The gel point was approximated by the G'/G" crossover time.

Rheological Properties of Single- and Dual-Crosslinked OMA/PEG Hydrogels

To fabricate dual-crosslinked OMA/PEG hydrogels, OMA and PEG solutions were prepared as described above. The mixed OMA/PEG solutions were injected between two glass plates separated by 0.75 mm spacers, incubated for 30 min, and then photocrosslinked with 365 nm UV light (Model EN-280L, Spectroline, Westbury, N.Y.) placed on top of the upper plate at ~1 mW/cm$^2$ for 15 min to form the dual-crosslinked hydrogels. Dual-crosslinked OMA/PEG hydrogel disks were created using an 8 mm diameter biopsy punch and placed in a humidified incubator at 37° C. for 30 min. As a comparative group, single-crosslinked OMA/PEG hydrogel disks were also prepared without photocrosslinking.

The rheological properties of the single- and dual-crosslinked OMA/PEG hydrogels were measured in terms of the storage (G') and the loss (G") moduli using a strain-controlled AR-2000ex rheometer (TA Instruments) using an 8 mm diameter stainless-steel parallel plate geometry with a 0.7-0.8 mm gap. Plate temperature was maintained at 25° C. After the 30 min incubation, the measurement was performed using a dynamic frequency sweep test in which a sinusoidal shear strain of constant peak amplitude (0.2%) was applied over a range of frequencies (0.6-100 rad/sec) (N=3).

Swelling Behavior, Degradation, and Mechanical Property Change of the OMA/PEG Hydrogels Over Time The single- and dual-crosslinked OMA/PEG hydrogel disks were prepared as described above and lyophilized, and dry weights ($W_i$) were measured. Dried hydrogel samples were immersed in 10 ml of DMEM and incubated at 37° C., and DMEM was replaced every week. At predetermined time points, samples were removed, rinsed with DMEM, and the swollen ($W_s$) hydrogel sample weights were measured. The swelling ratio (Q) was calculated by $Q = W_s/W_i$ (N=3 for each time point). After weighing the swollen hydrogel samples, the samples were lyophilized and weighed ($W_d$). The percent mass loss was calculated by $(W_i - W_d)/W_i \times 100$ (N=3 for each time point).

The dual-crosslinked OMA/PEG hydrogel disks were prepared and incubated as described above. At predetermined time points, the swollen dual-crosslinked OMA/PEG hydrogel disks were punched once again to match the diameter of the parallel plates (8 mm) The storage (G') and loss (G") moduli of the dual-crosslinked OMA/PEG hydrogels were measured using a dynamic frequency sweep test with a strain-controlled AR-2000ex rheometer as described above (N=3 for each time point).

Cytotoxicity of OMA/PEG Macromers and Dual-Crosslinked OMA/PEG Hydrogels

To evaluate potential cytotoxicity of the OMA/PEG macromers and the dual-crosslinked OMA/PEG hydrogels, an indirect contact methodology was employed. Briefly, a human bone marrow aspirate was harvested from the posterior iliac crest of a donor after informed consent under a protocol approved by the University Hospitals of Cleveland Institutional Review Board. The human bone marrow-derived mesenchymal stem cells (hMSCs) were isolated from the bone marrow aspirate and cultured in the Skeletal Research Center Mesenchymal Stem Cell Facility as previously described. hMSCs (passage number 2) were plated in 6-well tissue culture plates at $1 \times 10^5$ cells/well in 3 ml of DMEM containing 10 v/v % fetal bovine serum (FBS, Sigma) and cultured at 37° C. and 5% $CO_2$ for 24 hrs. Cell culture inserts (25 mm in diameter, 8 μm pore size on PET track-etched membrane; Becton Dickinson Labware Europe, Le Pont De Claix, France) were placed into each well. To prepared dual-crosslinked OMA/PEG hydrogels for cytotoxicity testing, OMA/PEG macromer solutions (200 μl) were pipetted into 96-well tissue culture plates and photocrosslinked with UV for 15 min. Sterile OMA/PEG macromer solution (200 μl) or a dual-crosslinked OMA/PEG hydrogel, was added into each culture insert. hMSCs cultured with a cell culture insert but without the presence of any macromer or hydrogel material were maintained as a comparative group. A control group, not exposed to any macromer, hydrogel material or insert, was maintained in parallel. After 48 hrs incubation, media, inserts and hydrogels were removed. Each well was rinsed with phosphate buffered saline (PBS), and 3 ml of a 20% CellTiter 96 Aqueous One Solution (Promega Corp., Madison, Wis., USA), which contains 3-[4,5-dimethylthiazol-2-yl]-5-[3-carboxymethoxy-phenyl]-2-[4-sulfophenyl]-2H-tetrazolium (MTS-tetrazolium), in PBS was added to each well. The MTS-tetrazolium compound can be metabolized by mitochondria in living cells into a colored formazan product that is soluble in cell culture medium. After incubating at 37° C. for 90 min, the absorbance of the solutions was determined at 490 nm using a 96-well plate reader (SAFIRE; Tecan, Austria) (N=5).

Adhesion Strength of OMA/PEG Hydrogels

Figure 6:
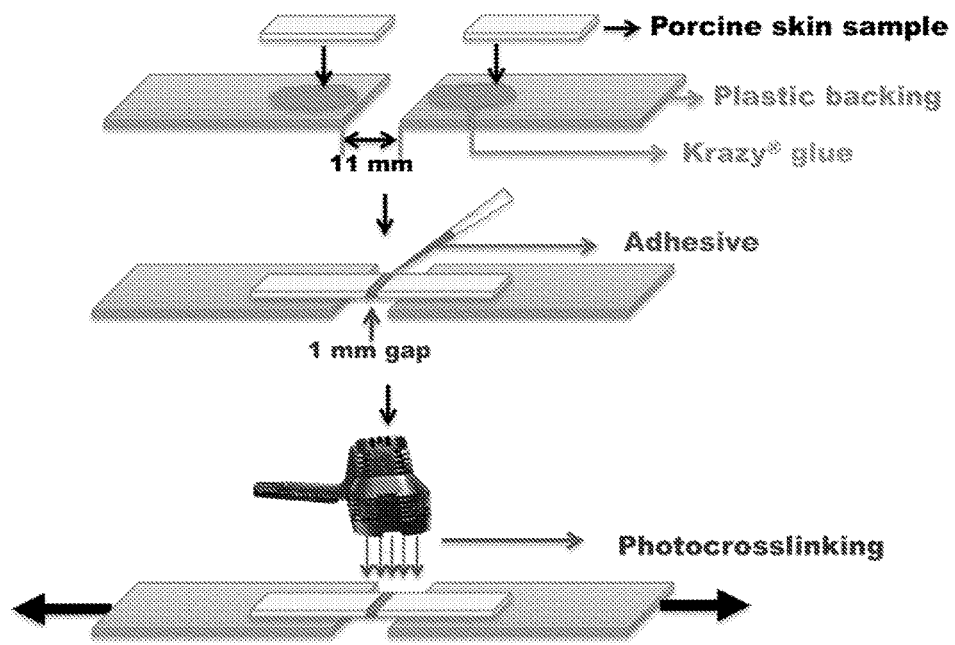
FIG. 6 illustrates schematic drawing of the test set-up used to determine adhesion strength of OMA/PEG bioadhesives.

To examine the bioadhesion strength of the hydrogels, porcine hide, with hair removed with a razor blade, was purchased from a local butcher shop and stored at 4° C. in Krebs-Ringer bicarbonate buffer solution (Sigma). Porcine skin tissue samples were cut into rectangular pieces with dimensions of $20 \times 10$ mm$^2$ after removing the subcutaneous layers using a surgical scalpel. As shown in FIG. 6, skin samples were attached to a plastic backing (a PET transparency film) using cyanoacrylate glue (Krazy Glue®, Elmer's Products Inc., Columbus, Ohio), and their thickness was measured using calipers. After attaching two skin tissue samples with a 1 mm gap, the OMA/PEG macromer solution (100 μl) was injected between two tissue specimens and cured in a humidified chamber at room temperature for 2 hrs 45 min after 15 min incubation at atmospheric condition. To compare the adhesion strength of single-crosslinked hydrogels with dual-crosslinked hydrogels, OMA-20/PEG group was photocrosslinked under UV at ~1 mW/cm$^2$ for 15 min, and the dual-crosslinked OMA-20/PEG group was further cured in a humidified chamber at room temperature for 2 hrs 45 min. As a comparative group, a commercially available fibrin bioadhesive (Tisseel®, Baxter Corporation) was prepared according to the manufacturer's instruction. The fibrin bioadhesive (100 μl) was also injected between two tissue specimens, incubated at atmospheric conditions for 15 min, and then cured in a humidified chamber at room temperature for 2 hrs 45 min. The adhesion strength of the bioadhesives was determined by performing constant strain rate tensile tests using a Rheometrics Solid Analyzer (RSAII, Rheometrics Inc., Piscataway, N.J., USA) equipped with a 10 N load cell. The plastic backings were loaded into the clamps of the mechanical tester, the cross-sectional areas of tissue specimens were measured using calipers, and tensile tests were performed on specimens at room temperature using a constant strain rate of 5%/sec. The adhesion strength is defined as the maximum load force observed in this measurement divided by the cross-sectional area of the porcine skin specimens (N=3).

Preparation of OMAs and OMA/PEG Hydrogels

To prepare dual-crosslinkable OMA macromers, sodium alginates were oxidized using sodium periodate, and then methacrylate groups were introduced onto the oxidized alginate backbone using carbodiimide chemistry. Oxidation of the alginate creates multiple dialdehyde groups throughout the alginate chains that enable a crosslinked network to form through relatively fast formation of imine bonds with the 8-arm PEG amines used in this study and also with amines of tissue proteins permitting adhesion. The overall strategy for dual-crosslinked OMA/PEG hydrogel bioadhesive formation is showed in FIG. 1. The first crosslinking networks are formed by Schiff base reaction between aldehyde groups of the OMA and amines of the 8-arm PEG and provide the cohesive force that stabilizes the bioadhesive into a hydrogel. The second crosslinking networks formed by photocrosslinking the methacrylate groups of OMA may provide an improved resistance to shear or tensile loading and excessive swelling.

Gelling Time of Single-Crosslinked OMA/PEG Bioadhesives

Oscillatory rheological experiments were performed to evaluate the time to gel formation of single-crosslinked OMA/PEG bioadhesives formed with OMAs with a range of aldehyde content. OMA and PEG solutions were quickly mixed and immediately applied to the rheometer where the mixed solutions were subjected to oscillatory time sweeps. Subsequently, the kinetics of the gel formation was determined by monitoring the storage (G') and loss (G") moduli for the forming hydrogels over time. As shown in FIG. 2A, both moduli for all conditions elevated as the gelation proceeded over time, indicating the formation of well-developed crosslinked three-dimensional networks. However, G' increased more rapidly than G" and became equal to G". The point at which G' becomes equal to G" is typically used as a gelling time ($t_{gel}$) [27]. As expected, the OMA-20/PEG ($t_{gel}$=4.9±0 4 min) exhibited faster gelation and higher resultant storage modulus (G') compared to the OMA-14/PEG ($t_{gel}$=8.0±0 3 min) due to the larger number of aldehyde groups of OMA-20 per 8-arm PEG amine (FIG. 2B). OMA-9/PEG showed the slowest gelation ($t_{gel}$=25.0±4.1 min) and the lowest G' since the OMA-9 had the least number of aldehyde groups available to react with the 8-arm PEG amines (FIG. 2B). Control over the degree of alginate oxidation permits regulation of the gelling time of the OMA/PEG bioadhesives as well as their mechanical properties, and this allows for tailoring of these bioadhesive properties depending on the clinical application.

Rheology of the OMA/PEG Bioadhesives

Figure 3:
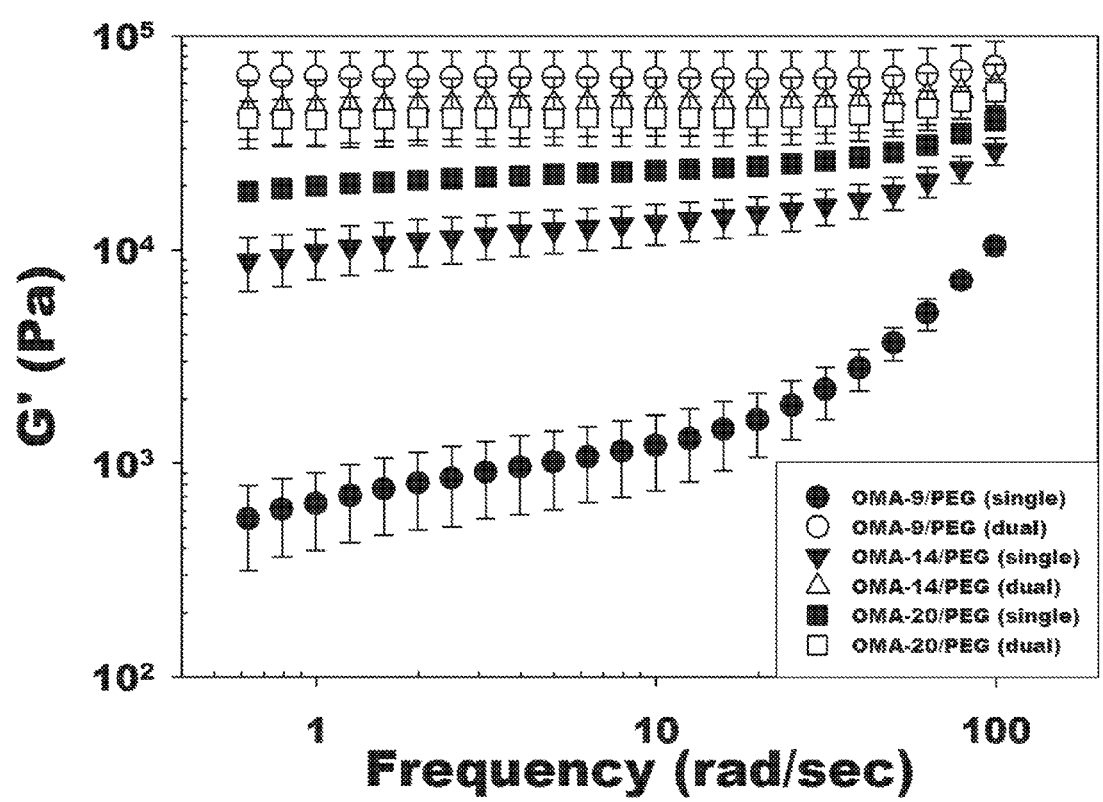
FIG. 3 illustrates a plot showing storage moduli (G') of the single- and dual-crosslinked OMA/PEG hydrogels by rheological measurements at day 0. Values represent mean±standard deviation (N=3).

Rheological experiments were also performed on the single- and dual-crosslinked OMA/PEG hydrogels to examine the effects of the degree of alginate oxidation and crosslinking on the hydrogel mechanical properties. Storage moduli (G') were plotted as a function of frequency, which were significantly ($p<0.05$) higher than loss moduli (G", data not shown) at all frequencies tested for all hydrogel groups. As shown in FIG. 3, the storage modulus of single-crosslinked OMA/PEG hydrogels increased with increasing alginate oxidation. This increase in storage modulus may be a result of increased aldehyde groups capable of reacting with the amines of the PEG. As the frequency increased from 0.6 to 100 rad/sec, a moderate increase of G' was observed for all single-crosslinked OMA/PEG hydrogels, indicating that the single-crosslinked OMA/PEG hydrogels are fairly viscoelastic, while all dual-crosslinked OMA/PEG hydrogels exhibited a plateau of G' in the range of 0.6 to 100 rad/sec, which indicates a more stable crosslinked network of hydrogel. However, there was no significant difference in G' between the dual-crosslinked OMA/PEG hydrogels. The dual-crosslinked OMA/PEG hydrogels also exhibited significantly greater G' than the single-crosslinked OMA/PEG hydrogels at all frequencies tested. This result indicates that for the specific conditions examined in this study (i.e., concentration of 8-arm PEG amine and degree of actual methacrylation), the storage modulus of OMA/PEG hydrogels was strongly enhanced by photocrosslinking after the chemical crosslinking. Since bioadhesives may be exposed to mechanical forces (i.e., shear and tensile force) in in vivo environments, the increased mechanical properties of the OMA/PEG hydrogels following photocrosslinking may contribute to improving their stability when used in such applications.

Swelling Kinetics, Degradation Profiles, and Storage Moduli Change Over Time of the OMA/PEG Bioadhesives The effect of altering the degree of alginate oxidation on the single- and dual-crosslinked OMA/PEG hydrogel swelling behavior, degradation, and mechanical properties over time was examined, as these properties are important for bioadhesive functionality. As shown in FIG. 4A, all single-crosslinked OMA/PEG hydrogels displayed rapid swelling kinetics. The swelling of single-crosslinked OMA-14/PEG and OMA-20/PEG hydrogels increased up to 2 and 3 days, respectively, and then rapidly decreased as the hydrogels degraded. Compared to the OMA-14/PEG and OMA-20/PEG, OMA-9/PEG hydrogels exhibited much faster swelling kinetics. The swelling of OMA-9/PEG hydrogels reached a maximum by 12 h and then rapidly decreased. All single-crosslinked OMA/PEG hydrogels underwent complete degradation within 7 days (FIG. 4B). Degradation of the single-crosslinked OMA/PEG hydrogels depended on the degree of alginate oxidation. As the alginate oxidation level increased from 9% to 20%, the degradation rate of the single-crosslinked OMA/PEG hydrogels decreased. Increased oxidation of the alginate creates more available aldehyde groups in the OMA to form unstable imine bonds with the free PEG amines. Increased crosslinking retards swelling and degradation until these crosslinks are hydrolyzed.

All dual-crosslinked OMA/PEG hydrogels reached equilibrium swelling rapidly within 1 day and then the dual-crosslinked OMA-9/PEG and OMA-14/PEG hydrogels gradually increased over the course of 4 weeks (FIG. 4C). The equilibrium swelling ratio after 1 day increased with increasing degree of alginate oxidation. Compared to the dual-crosslinked OMA-9/PEG and OMA-14/PEG hydrogels, the swelling of the dual-crosslinked OMA-20/PEG hydrogels rapidly decreased after 2 weeks due to their almost complete degradation by 3 weeks. As shown in FIG. 4D, the dual-crosslinked OMA/PEG hydrogels displayed slower degradation compared to the single-crosslinked hydrogels. Among the dual-crosslinked hydrogels, the OMA-20/PEG hydrogels exhibited the fastest degradation rate with complete degradation by 3 weeks, while the OMA-14/PEG and OMA-9/PEG hydrogels had relatively similar degradation rates, which were slower than that of OMA-20/PEG hydrogels (FIG. 4D). The dual-crosslinked OMA/PEG hydrogels are expected to degrade by hydrolysis of both the alginate backbone and the two types of crosslinks in the system. The unstable imine bond crosslinks likely degrade most rapidly, followed by the alginate backbone and ester bonds in the photocrosslinks. Due to the similar methacrylation degree of oxidized alginates, the degradation of the dual-crosslinked OMA/PEG may be mainly affected by degree of alginate oxidation as increased oxidation can increase the alginate's susceptibility to hydrolysis.

Changes in the storage moduli of the OMA/PEG hydrogel bioadhesives were monitored to examine the correlation between mechanical property changes and alginate oxidation level during degradation because these changes with respect to the mechanical properties and environment of the surrounding tissues can influence their success in some clinical applications. Dynamic mechanical analysis was performed on the dual-crosslinked OMA-9/PEG and OMA-14/PEG hydrogels during the degradation study to quantify their storage moduli. As shown in FIG. 3, there was no significant difference in initial storage moduli at day 0 between these two dual-crosslinked hydrogels (open circles and open triangles). The storage moduli of the dual-crosslinked OMA-9/PEG (FIG. 4E) and OMA-14/PEG (FIG. 4F) hydrogels decreased during the course of degradation and were predominantly independent of frequency. When comparing the rate of change in storage modulus, it is apparent that the storage modulus of the dual-crosslinked OMA-14/PEG hydrogels decreased more rapidly than that of the dual-crosslinked OMA-9/PEG hydrogels likely due to the higher degree swelling of the former (FIG. 4C).

Cytotoxicity of the OMA/PEG Bioadhesives

The potential cytotoxicities of OMA and PEG macromers and dual-crosslinked hydrogels were evaluated by measuring the mitochondrial metabolic activity of hMSCs cultured on tissue culture plastic in the presence of the biomaterials using a standard MTS assay. Cell viability after 48 hrs culture was calculated by normalizing the absorbance of samples at 490 nm to that of a control without any macromers, hydrogel or insert in the medium. The viability of cells cultured in the presence of OMA/PEG macromers and the dual-crosslinked hydrogels decreased as the alginate oxidation level increased (FIG. 5). There was no significant difference between the mitochondrial activity of hMSCs cultured with OMA-9/PEG and OMA-14/PEG macromers (FIG. 5A), the dual-crosslinked OMA-9/PEG and OMA-14/PEG hydrogels (FIG. 5B), and the dual-crosslinked OMA-14/PEG and OMA-20/PEG hydrogels (FIG. 5B). Biomaterials and their degradation byproducts must be cytocompatible for biomedical applications. As determined by the MTS assay, the viability of hMSCs in monolayer culture following exposure to OMA/PEG macromers and the dual-crosslinked OMA/PEG hydrogels was at least 67% for the OMA-20/PEG macromers and as high as 93% for the OMA-9/PEG hydrogels compared to controls, which indicates a fairly cytocompatible and non-toxic nature of the hydrogel biomaterials and their degradation byproducts.

Adhesion Strength of the OMA/PEG Bioadhesives

Figure 7:
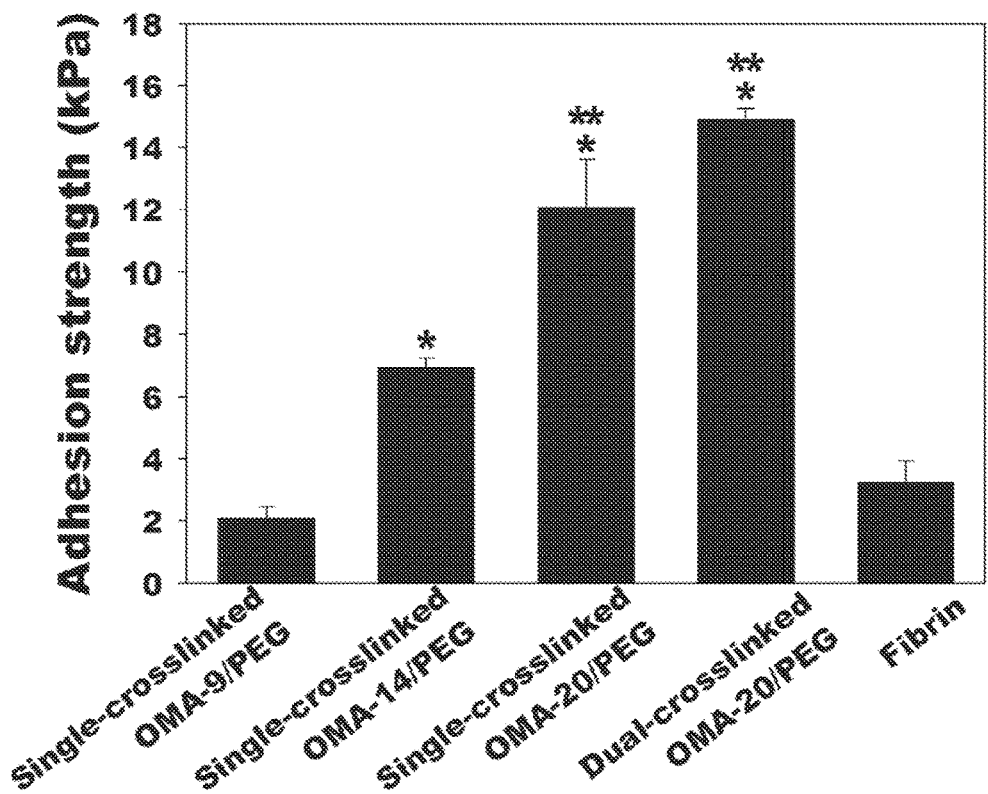
FIG. 7 illustrates a graph showing the adhesion strength of the single-crosslinked OMA/PEG bioadhesives, dual-crosslinked OMA-20/PEG bioadhesives, and fibrin. Values represent mean±standard deviation (N=3). *p<0.05 compared with single-crosslinked OMA-9 and fibrin. **p<0.05 compared with single-crosslinked OMA-14/PEG bioadhesive.

Tensile tests of the single-crosslinked and dual-crosslinked hydrogels were performed to determine their adhesion strength to porcine skin and results were compared to the adhesion strength of commercially available fibrin glue. As shown in FIG. 7, the adhesion strength of single-crosslinked OMA/PEG hydrogels increased as the oxidation level of alginate increased from 9% to 20%. There was no significant difference between the adhesion strength of the OMA-9/PEG hydrogels and fibrin glue. However, the OMA-14/PEG and OMA-20/PEG hydrogels exhibited significantly higher adhesion strength than fibrin glue. Since the OMA/PEG hydrogels adhere to tissue through the interaction between aldehyde groups in the bioadhesive and amine groups of tissue, controlled modulation of the OMA/PEG hydrogel aldehyde concentration could be employed to optimize the bioadhesive for various tissues, which have different amine densities. To evaluate the effect of photocrosslinking on the adhesion strength of OMA/PEG hydrogels, the adhesion strength of the dual-crosslinked OMA-20/PEG hydrogels was also measured and compared with the single-crosslinked OMA-20/PEG hydrogels. There was no significant difference in the adhesion strength between single- and dual-crosslinked hydrogels, indicating that the most desirable physical properties can be selected from these two types of hydrogels for a specific application without compromising adhesion strength.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, I claim:

1. A bioadhesive comprising: a crosslinked biodegradable hydrogel that includes a plurality of oxidized and acrylated or methacrylated natural polymer macromers crosslinked with a plurality of branched poly(ethylene glycol) macromers, wherein the bioadhesive upon application to injured tissue mechanically joins or seals the injured tissue.

2. The bioadhesive of claim 1, wherein the oxidized and acrylated or methacrylated natural polymer macromers include a plurality of aldehyde groups that are crosslinked with the branched poly(ethylene glycol) macromers.

3. The bioadhesive of claim 1, wherein the oxidized and acrylated or methacrylated natural polymer macromers are polysaccharides, which are oxidized so that about 1% to about 50% of the saccharide units therein are converted to aldehyde saccharide units.

4. The bioadhesive of claim 1, wherein acrylate or methacrylate groups of the natural polymer macromers are crosslinked so that the hydrogel is dual crosslinked.

5. The bioadhesive of claim 1, the oxidized and acrylated or methacrylated natural polymer macromers comprise oxidized and acrylated or methacrylated alginates.

6. The bioadhesive of claim 1, wherein the poly(ethylene glycol) macromers are poly(ethylene glycol) amine macromers.

7. The bioadhesive of claim 6, wherein the poly(ethylene glycol) amine macromers are n-arm poly(ethylene glycol) amines, where n is an integer greater than 1.

8. The bioadhesive of claim 1, wherein the hydrogel is cytocompatible and, upon degradation, produces substantially non-toxic products.

9. The bioadhesive of claim 1, wherein the hydrogel is photocrosslinked.

10. A bioadhesive comprising: a dual crosslinked biodegradable hydrogel that includes a plurality of oxidized and acrylated or methacrylated polysaccharide macromers crosslinked with a plurality of branched poly(ethylene glycol) macromers, wherein the bioadhesive upon application to injured tissue mechanically joins or seals the injured tissue.

11. The bioadhesive of claim 10, wherein the oxidized and acrylated or methacrylated polysaccharide macromers include a plurality of aldehyde groups that are crosslinked with the branched poly(ethylene glycol) macromers.

12. The bioadhesive of claim 10, wherein the oxidized and acrylated or methacrylated polysaccharide macromers are polysaccharides, which are oxidized so that about 1% to about 50% of the saccharide units therein are converted to aldehyde saccharide units.

13. The bioadhesive of claim 10, wherein acrylate or methacrylate groups of the polysaccharide macromers are cross-linked.

14. The bioadhesive of claim 10, the oxidized and acrylated or methacrylated polysaccharide macromers comprise oxidized and acrylated or methacrylated alginates.

15. The bioadhesive of claim 10, wherein the poly(ethylene glycol) macromers are poly(ethylene glycol)amine macromers.

16. The bioadhesive of claim 15, wherein the poly(ethylene glycol) amine macromers are n-arm poly(ethylene glycol) amines, where n is an integer greater than 1.

17. The bioadhesive of claim 10, wherein the hydrogel is cytocompatible and, upon degradation, produces substantially non-toxic products.

18. A bioadhesive comprising: a dual crosslinked biodegradable hydrogel that includes a plurality of oxidized and acrylated or methacrylated alginate macromers crosslinked with a plurality of branched poly(ethylene glycol) macromers, wherein the bioadhesive upon application to injured tissue mechanically joins or seals the injured tissue.

19. The bioadhesive of claim 18, wherein the oxidized and acrylated or methacrylated alginate macromers include a plurality of aldehyde groups that are crosslinked with the branched poly(ethylene glycol) macromers.

20. The bioadhesive of claim 18, wherein the oxidized and acrylated or methacrylated alginate macromers is an aliginate, which is oxidized so that about 1% to about 50% of the saccharide units therein are converted to aldehyde saccharide units.

21. The bioadhesive of claim 18, wherein acrylate or methacrylate groups of the alignate macromers are photocrosslinked.

22. The bioadhesive of claim 18, wherein the poly(ethylene glycol) macromers are poly(ethylene glycol)amine macromers.

23. The bioadhesive of claim 22, wherein the poly(ethylene glycol) amine macromers are n-arm poly(ethylene glycol) amines, where n is an integer greater than 1.

24. The bioadhesive of claim 18, wherein the hydrogel is cytocompatible and, upon degradation, produces substantially non-toxic products.

\* \* \* \* \*